United States Patent
Kiraly et al.

(10) Patent No.: US 9,173,626 B2
(45) Date of Patent: Nov. 3, 2015

(54) METHOD FOR PERFORMING DYNAMIC REGISTRATION, OVERLAYS, AND 3D VIEWS WITH FLUOROSCOPIC IMAGES

(71) Applicants: Atilla Peter Kiraly, Plainsboro, NJ (US); Wen Wu, East Windsor, NJ (US); Norbert Strobel, Heroldsbach (DE); Alexander Benjamin Brost, Erlangen (DE); Terrence Chen, Princeton, NJ (US)

(72) Inventors: Atilla Peter Kiraly, Plainsboro, NJ (US); Wen Wu, East Windsor, NJ (US); Norbert Strobel, Heroldsbach (DE); Alexander Benjamin Brost, Erlangen (DE); Terrence Chen, Princeton, NJ (US)

(73) Assignee: Siemens Aktiengesellschaft, Munich (DE)

( * ) Notice: Subject to any disclaimer, the term of this patent is extended or adjusted under 35 U.S.C. 154(b) by 218 days.

(21) Appl. No.: 13/733,395

(22) Filed: Jan. 3, 2013

(65) Prior Publication Data
US 2013/0172732 A1    Jul. 4, 2013

Related U.S. Application Data

(60) Provisional application No. 61/582,974, filed on Jan. 4, 2012.

(51) Int. Cl.
*A61B 5/05*    (2006.01)
*A61B 6/00*    (2006.01)
*A61B 6/12*    (2006.01)
*A61M 25/00*   (2006.01)

(52) U.S. Cl.
CPC ............... *A61B 6/5241* (2013.01); *A61B 6/12* (2013.01); *A61B 6/469* (2013.01); *A61B 6/485* (2013.01); *A61B 6/503* (2013.01); *A61B 6/504* (2013.01); *A61B 6/5235* (2013.01); *A61B 6/5264* (2013.01); *A61M 25/0068* (2013.01); *A61B 6/466* (2013.01)

(58) Field of Classification Search
CPC ........ A61B 6/5241; A61B 6/12; A61B 6/485; A61B 6/503; A61B 6/504; A61B 6/466; A61B 6/469; A61M 25/0068
USPC ....................................................... 600/424
See application file for complete search history.

(56) References Cited

U.S. PATENT DOCUMENTS

2009/0163800 A1 *  6/2009  Xu et al. ............... 600/424
2010/0324413 A1 * 12/2010  Tetsuka et al. ......... 600/424

OTHER PUBLICATIONS

Brost et al., 3-D Respiratory Motion Compensation during EP Procedures by Image-Based 3-D Lasso Catheter Model Generation and Tracking, MICCAI 2009, Part I, LNCS 5761, pp. 394-401, 2009.*
Brost et al., Respiratory motion compensation by model-based catheter tracking during EP procedures, Medical Image Analysis, 14, 2010, 695-706.*
Brost et al., Catheter Tracking: Filter-Based vs. Learning-Based, DAGM 2010, LNCS 6376, pp. 293-302, 2010.*
M. Haissaguerre, L. Gencel, B. Fischer, P. Le Metayer, F. Poquet, F. I. Marcus, and J. Clementy, "Successful Catheter Ablation of Atrial Fibrillation," J. Cardiovasc Electrophysiol 1994, pp. 1045-1052, vol. 5.

(Continued)

*Primary Examiner* — Bo J Peng

(57) ABSTRACT

A method (200, 300) and system (100) for performing real-time, dynamic overlays on fluoroscopic images to aid in navigation and localization during medical procedures.

7 Claims, 6 Drawing Sheets

(56) References Cited

OTHER PUBLICATIONS

F. Bourier, F. Heisenhuber, HJ. Schneider, P. Ganslmeier, R. Fischer, A. Brost, M. Koch, N. Strobel, J. Hornegger, and K. Kurzidim, "3D-Funktionalitat und Navigation durch einen Siemens-Prototypen in der biplanen Fluoroskopie zur Pulmonalvenenisolation," Deutsche Gesellschaft fur Kordiologie, Jahrestagung, 2011, Mannheim.

F. Bourier, HJ. Schneider, P. Ganslmeier, F. Heisenhuber, R. Fischer, A. Brost, M. Koch, N. Strobel, J. Hornegger, and K. Kurzidim, "Unterstuetzung der transseptalen Punktion durch vorherige Oberlagerung eines 3D-Volumens von linkem Atrium und Aorta," Deutsche Gesellschaft fur Kordiologie, Jahrestagung, 2011, Mannheim.

L. Gepstein, G. Hayam, and S. A. Ben-Haim, "A Novel Method for Nonfluoroscopic Catheter-Based Electroanatomical Mapping of the Heart: In Vitro and In Vivo Accuracy Results," Circulation, 1997, pp. 1611-1622, vol. 95.

A. Brost, A. Wimmer, R. Liao, J. Hornegger, and N. Strobel, "Catheter Tracking; Filter-Based vs. Learning-Based," in Pattern Recognition, M. Goesele, S. Roth, A. Kuijper, B. Schiele, and K. Schindler, Eds., Lecture Notes in Computer Science 6376, 2010, pp. 293-302, Springer, Berlin/Heidelberg.

W. Wu, T. Chen, A. Barbu, P. Wang, N. Strobel, S. K. Zhou, and D. Comaniciu, "Learning-based Hypothesis Fusion for Robust Catheter Tracking in 2D X-ray Fluoroscopy," IEEE Conference on Computer Vision and Pattern Recognition (CVPR), 2011, pp. 1097-1104.

Alexander Brost, Wen Wu, Martin Koch, Andreas Wimmer, Terrence Chen, Rui Liao, Joachim Hornegger, and Norbert Strobel, "Combined Cardiac and Respiratory Motion Compensation for Atrial Fibrillation Ablation Procedures", Med Image Comput Comput Assist Interv. (MICCAI) 2011, pp. 540-547, 14(Pt. 1).

Liron Yatziv, Julian Ibarz, Norbert Strobel, Saurabh Datta, and Guillermo Sapiro, "Esophagus Silhouette Extraction and Reconstruction From Fluoroscopic Views for Cardiac Ablation Procedure Guidance", IEEE Transactions on Information Technology in Biomedicine, 2011, pp. 703-708, vol. 15 (No. 5).

\* cited by examiner

US 9,173,626 B2

METHOD FOR PERFORMING DYNAMIC REGISTRATION, OVERLAYS, AND 3D VIEWS WITH FLUOROSCOPIC IMAGES

CROSS-REFERENCE TO RELATED APPLICATIONS

This application claims the benefit of Provisional U.S. Patent Application Ser. No. 61/582,974 entitled, "Method And Interface For Dynamic Registration, Overlays, And 3D Views With Fluoroscopic Images", filed in the name of Atilla Peter Kiraly, Wen Wu, Norbert Strobel, Alexander Benjamin Brost, and Terrence Chen, on Jan. 4, 2012, the disclosure of which is also hereby incorporated herein by reference.

FIELD OF INVENTION

The present invention relates to medical fluoroscopic imaging. More particularly, the present invention relates to providing dynamic image overlays for fluoroscopic anatomical images used in medical procedure guidance.

BACKGROUND OF THE INVENTION

Heart arrhythmia are usually caused by improper or abnormal coordination of electrical impulses in a patient's heart. They can present themselves as a fast, slow, or irregular heart beat. Electrophysiology (EP) procedures or studies, such as radio frequency ablation (RFA), are conducted by cardiac medical specialists to help diagnose and treat these abnormal heart rhythms of patients. This is generally described in an article by M. Haissaguerre, L. Gencel, B. Fischer, P. Le Metayer, F. Poquet, F. I. Marcus, and J. Clementy, entitled "Successful Catheter Ablation of Atrial Fibrillation," J. Cardiovasc Electrophysiol, 1994, pp. 1045-1052, Vol. 5.

At the beginning of an EP procedure, a catheter is inserted into a blood vessel near the groin of a patient and guided to the heart. The specialist will use specialized EP procedure tools to then conduct heart rhythm tests and, if warranted, treatment. Specifically, RFA is a treatment that heats the heart tissue to the point of causing lesions that will block certain electrical pathways in the heart tissue that are contributing to an arrhythmia. Ablation treatment decisions by the specialist can either be based on electrical signals (e.g., flutter, AVNRT) or on anatomy, respectively. In particular, treatment of atrial fibrillation (Afib) is based on anatomy, because specific sections of the pulmonary veins are primary ablation targets. Ablation treatment itself may be carried out using an irrigated ablation catheter.

Such ablation and other EP procedures are routinely conducted under image guidance, for example, using monoplane and bi-plane X-ray fluoroscopy, to provide visualization and localization of both a patient's anatomy and the respective EP procedure tools. In the case of RFA, this allows the specialist to target ablation points within the heart. Ablations lesions are usually set by applying radio-frequency energy to endocardial tissue or even epicardial heart tissue. Recently, an augmented fluoroscopy system has been developed that is capable of overlaying image information involving the heart and targeted ablation locations from pre-operative image data for additional guidance. The system specifically is capable of fusing properly rendered 3D anatomical heart information, as well as planned ablation locations, with 2D fluoroscopy projections for enhanced guidance during EP procedures. This is detailed in a first article by F. Bourier, F. Heisenhuber, H J. Schneider, P. Ganslmeier, R. Fischer, A. Brost, M. Koch, N. Strobel, J. Hornegger, and K. Kurzidim, entitled "3D-Funktionalitat und Navigation durch einen Siemens-Prototypen in der biplanen Fluoroskopie zur Pulmonalvenenisolation," Deutsche Gesellschaft fur Kordiologie, Jahrestagung, 2011, Mannheim, and a second article by F. Bourier, H J. Schneider, P. Ganslmeier, F. Heisenhuber, R. Fischer, A. Brost, M. Koch, N. Strobel, J. Hornegger, and K. Kurzidim, entitled "Unterstuetzung der transseptalen Punktion durch vorherige Oberlagerung eines 3D-Volumens von linkem Atrium und Aorta," Deutsche Gesellschaft fur Kordiologie, Jahrestagung, 2011, Mannheim, each of which is incorporated by reference herein. The 3D data may involve pre-operative magnetic resonance images (MRI) or computed tomography (CT) images of a patient's heart.

A pre-operative 3D magnetic resonance (MR) or computed tomography (CT), or C-arm computed tomography (CACT), image of the patient's chest can offer important insights into a patient's heart anatomy. This pre-operative data can be used to provide additional information during the respective EP procedure by overlaying 2D perceptive renderings of the 3D data upon the intra-operative fluoroscopic images. However, although useful, such overlay image information offers only approximate guidance because of intra-operative heart beating motions, breathing motions, and catheter motions. It would be advantageous to dynamically update the overlay image information in order to account for these motions.

SUMMARY OF THE INVENTION

An embodiment of the invention obviates the above problems by providing a method of registration of image overlays for anatomical images, comprising obtaining dynamic images of an anatomical region of interest; providing a static image of the anatomical region of interest; performing a rigid registration of the static image with the dynamic images using a lasso catheter secured to an object within the anatomical region of interest; estimating motion of the anatomical region of interest in the dynamic images using the lasso catheter; and dynamically updating registration of the images using the motion estimation. Obtaining dynamic images may comprise obtaining dynamic fluoroscopy images with corresponding projection geometry for each image of the anatomical region of interest. Providing a static image may comprise providing a segmented volumetric image of the anatomical region of interest. In such case, providing a static image may further comprise marking points of interest of the anatomical region of interest.

The lasso catheter may be secured to an object within the anatomical region of interest so as to move in synchronization with the anatomical region of interest and estimating may comprise estimating motion of the lasso catheter. In such case, estimating motion of the lasso catheter may comprise tracking movement of the lasso catheter and approximately calculating positional changes of the lasso catheter. Tracking may comprise marking electrodes on the lasso catheter. Dynamically updating may comprise dynamically updating registration of the images using the motion estimation of the lasso catheter to revise registration based on the approximately calculated positional changes of the lasso catheter.

The anatomical region of interest may comprise the heart and surrounding vasculature and the lasso catheter may be secured to a pulmonary vein. In such case, the lasso catheter may be secured to a pulmonary vein so as to move in synchronization with the heart and estimating motion of the heart may comprise estimating motion of the lasso catheter. Then, estimating motion of the lasso catheter may comprise tracking movement of the lasso catheter and approximately calculating positional changes of the lasso catheter. Tracking may comprise marking electrodes on the lasso catheter. Dynamically updating may comprise dynamically updating registration of the images using the motion estimation of the lasso catheter to revise registration based on the approximately calculated positional changes of the lasso catheter.

An embodiment of the invention may also provide a method of dynamically updating overlay images on fluoroscopic images to aid in medical procedures, comprising securing a lasso catheter to a first anatomical structure that allows the lasso catheter to move in synchronization with a second anatomical structure; performing a rigid registration of an overlay image with real-time fluoroscopic images of the first and second anatomical structures using the lasso catheter; tracking movement of the lasso catheter and the real-time fluoroscopic images of the first and second anatomical structures and estimating the motion of the lasso catheter and the real-time fluoroscopic images of the first and second anatomical structures; determining from the tracking and estimating step whether or not there are significant movements or significant shape changes, or both, of the lasso catheter that indicate the lasso catheter is no longer secured to the first anatomical structure; and stopping tracking and estimating if it is determined there are significant movements or significant shape changes, or both, of the lasso catheter that indicate the lasso catheter is no longer secured to the first anatomical structure, and updating registration of the overlay image with the real-time fluoroscopic images if it is determined there are not significant movements or significant shape changes, or both, of the lasso catheter that indicate the lasso catheter is no longer secured to the first anatomical structure.

The first anatomical structure may comprise a pulmonary vein and the second anatomical structure may comprise the heart. The overlay image may comprise a segmented 3D volume of the first and second anatomical structures and the real-time fluoroscopic images may comprise bi-plane real-time fluoroscopic images of the first and second anatomical structures. Tracking may comprise marking electrodes of the lasso catheter and tracking the electrodes within the real-time fluoroscopic images using a model-based approach. Estimating may comprise evaluating positional shifts of the lasso catheter.

The overlay image may be returned to a default position relative to the real-time fluoroscopic images upon stopping tracking and estimating. Significant movements or significant shape changes may comprise movements or shape changes outside a predetermined region of a real-time fluoroscopic image. The method may further comprise continuing the steps of tracking and estimating, determining, and stopping and updating upon updating registration of the overlay image with the real-time fluoroscopic images.

An embodiment of the invention may also provide a method of overlaying image information, comprising providing a real-time 3D image of an object; overlaying 2D image information onto the real-time 3D image; and dynamically adjusting the 2D image information to account for motions of the real-time 3D image. Dynamically adjusting may comprise updating the overlaying 2D information based on estimations of motions of the real-time 3D image. Also, the real-time 3D image may comprise a live fluoroscopic image and the 2D image information may comprise 2D perceptive renderings of 3D image information.

An embodiment of the invention may also provide a system of providing image guidance for medical procedures, comprising an imager that acquires fluoroscopic images of an anatomical structure of a patient and a processor that manipulates the images and other image data to produce image overlays for the fluoroscopic images that are dynamically adjusted to compensate for motion of the anatomical structure within the fluoroscopic images using motion estimations of a lasso catheter positioned in a patient to be in synchronization with the anatomical structure. The processor may manipulate the dynamically-adjusted image overlays and the fluoroscopic images to produce visualizations of the anatomical structure with an anatomical structure—centric coordinate system that is adapted to dynamically change and to inhibit views of movements by the patient.

DESCRIPTION OF THE DRAWINGS

For a better understanding of the present invention, reference is made to the following description of an exemplary embodiment thereof, and to the accompanying drawings, wherein.

DETAILED DESCRIPTION

Figure 1:
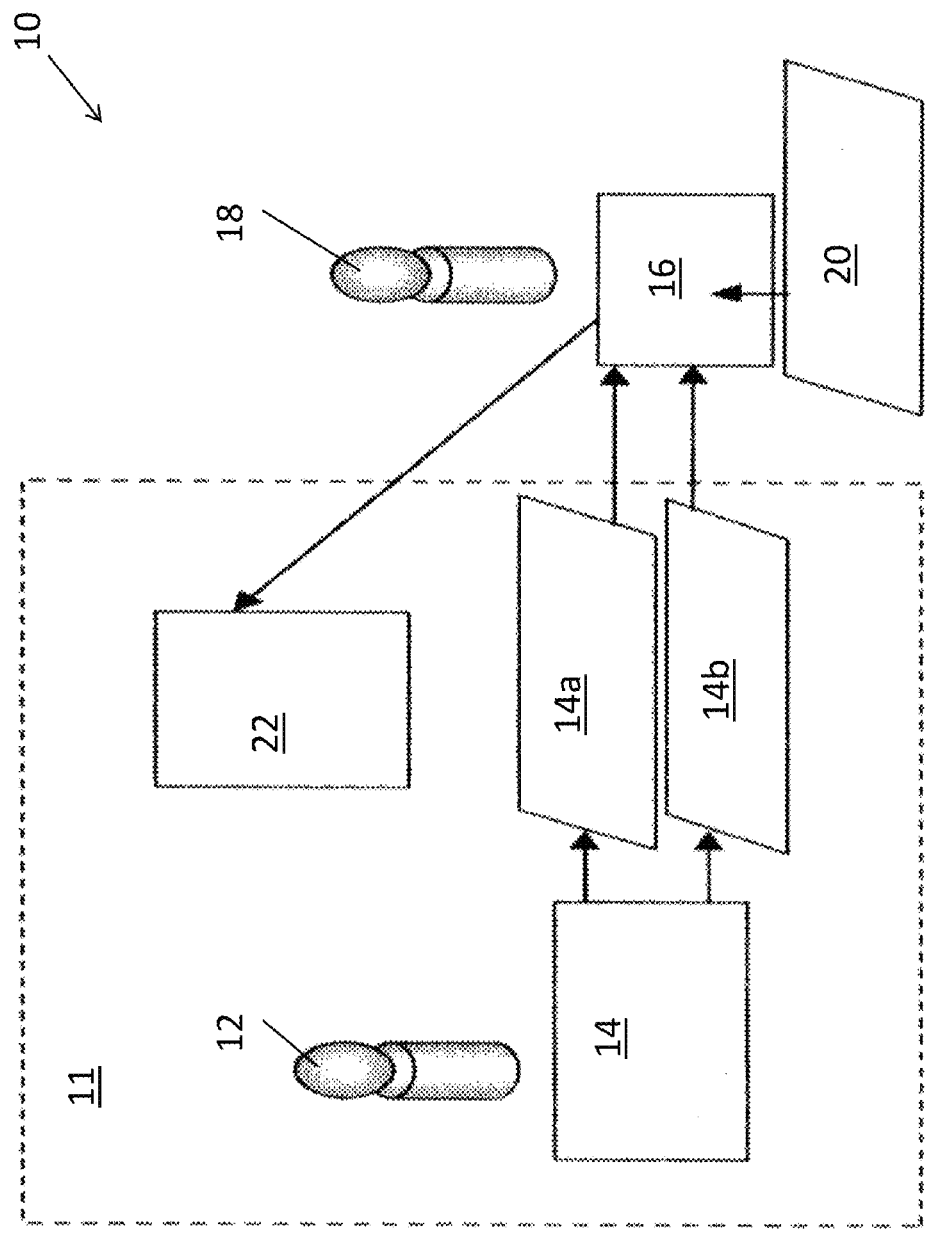
FIG. 1 is a schematic illustration of an overview for fluoroscopy-based navigation assistance in accordance with embodiments of the present invention.

FIG. 1 is a schematic illustration of an overview for fluoroscopy-based navigation assistance in accordance with embodiments of the present invention. The figure shows elements and operations of a medical imaging system 10 that may provide such navigation assistance. Briefly, in an operating room 11 for a respective medical procedure, health professionals 12 operate a medical imaging scanner 14 of the imaging system 10 that acquires intra-operative image data of an anatomical region of a patient under examination, for example, the heart of the patient. The scanner 14 may use X-ray imaging (e.g. using fluoroscopy), such as provided by a C-arm X-ray device/system. The images 14a and associated data conveying projection geometry parameters 14b of the projection system are sent to control and processing elements 16 of the fluoroscopy system 10. Outside of the operating room 11, an operator 18 assisting the health professionals 12 marks and highlights specific points in pre-operative volumetric image data 20 of the patient. Two-dimensional fluoroscopic overlay images 22 can then be rendered from the 3D data and be displayed in the operating room 11. As detailed below, the fluoroscopy system 10 can use lasso catheter tracking during the medical procedure to dynamically update the fluoroscopic overlay images 22.

Figure 2:
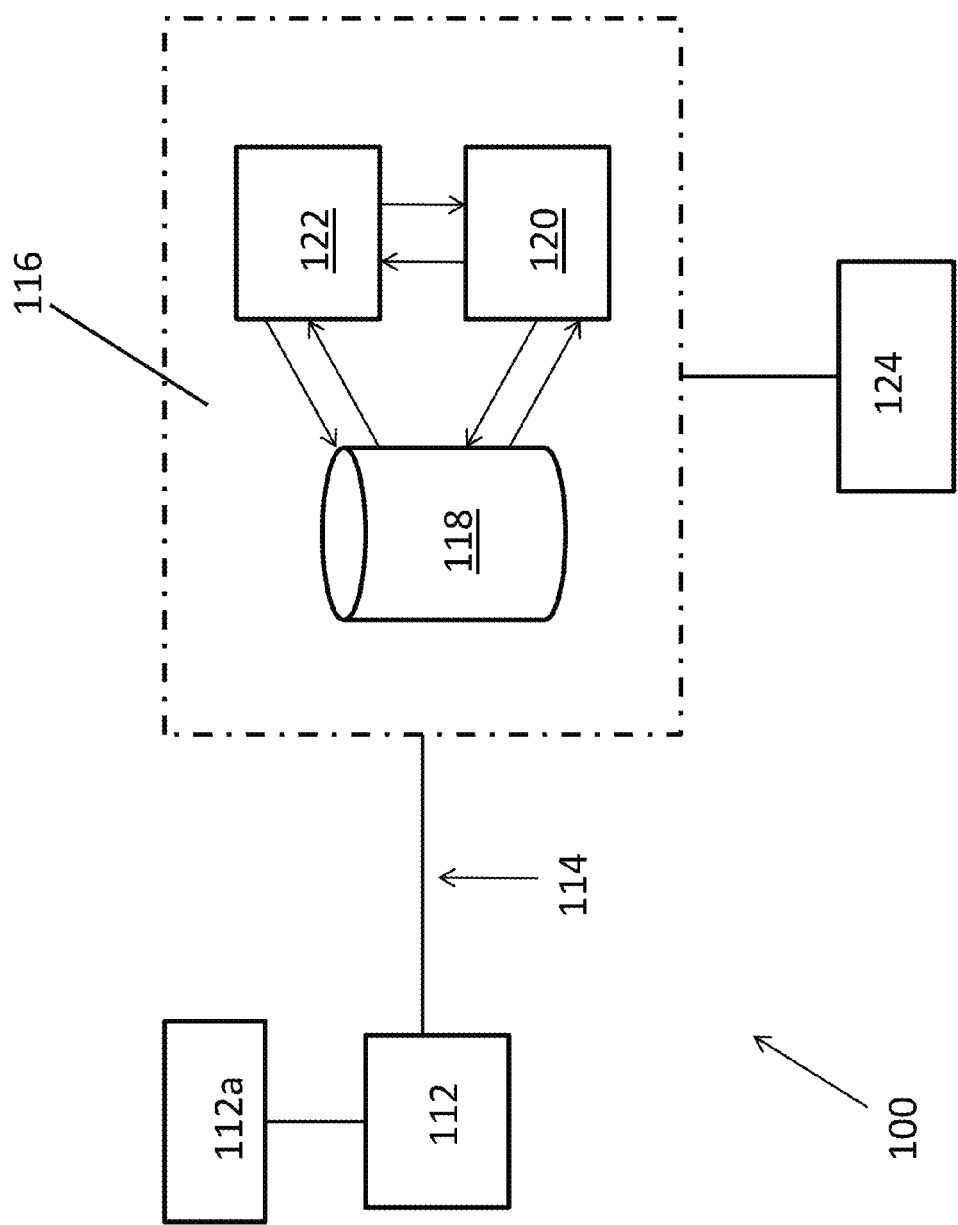
FIG. 2 is a block diagram of a medical imaging system (simplified) that may implement fluoroscopy-based navigation assistance in accordance with embodiments of the present invention.

FIG. 2 is a block diagram of a medical imaging system 100 (simplified) itself that may implement fluoroscopy-based navigation assistance in accordance with embodiments of the present invention. The system 100 comprises a medical imaging scanner 112 that acquires image data of a patient under examination, for example, of the heart of the patient. As noted above, the scanner 112 may use X-ray imaging (e.g. using fluoroscopy) or other appropriate imaging modality to acquire the image data such as fluoroscopy sequences, 3D datasets (C-arm CT imaging), and 2D DSA sequences. The scanner 112 may acquire raw image data from multiple scanned views of the region of interest of the patient, record or reconstruct the images, and produce image data signals for the multiple views. This may be done in real-time or near real-time. The image data signals may be in Digital Imaging and Communications in Medicine (DICOM) format. Other formats may also be used.

The imaging scanner 112 is operably connected to a computer system 112a that controls the operation of the scanner 112 and, via a communication channel 114, to an image processing system 116 that processes the image data signals utilizing appropriate image processing software applications. The image processing system 116 has an image data archive or database 118, an application server 120, and a user workstation 122. The components of the image processing system 116 are interconnected via a communications network that may be implemented by physical connections, wireless communications, or a combination. The image data archive or database 118 is adapted to store the image data signals that are produced by the image scanner 112 as well as the results of any additional operations on the image data signals by the other components of the image processing system 116. The image data archive or database 118 is also adapted to store pre-acquired imaging data (obtained via any appropriate imaging modality) or models of the anatomy or region of interest. The image data archive or database 118 may be a Picture Archiving and Communications System (PACS). Other types of image data archives or databases may also be used.

The user workstation 122 is adapted to control the operation of the imaging processing system 116 and its various components. The user workstation 122 particularly operates the application server 120 and the various image processing software applications that are stored in, or are accessible by, the server 120. The application server 120 also manages and coordinates the image data sets among the image processing applications. The image processing applications may include, for example, visualization applications, computer-aided diagnosis (CAD) applications, medical image rendering applications, anatomical segmentation applications, image registration applications, or any other type of medical image processing application. The image processing applications may also include embodiments of methods that are carried out in accordance with the present invention and those of the respective various steps. The image data archive or database 118, applications server 120, and the user workstation 122 may also each be connected to a remote computer network 124 for communication purposes or to access additional data or functionality. The workstation 122 may comprise appropriate user interfaces, like displays, storage media, input/output devices, etc.

The various components of the imaging system 100 are conventional and well known components. They may be configured and interconnected in various ways as necessary or as desired. The imaging system 100 and, in particular, the image processing system 116 is adapted to permit the imaging system 100 to operate and to implement methods in accordance with embodiments of the invention, for example, as shown and described below.

Figure 3:
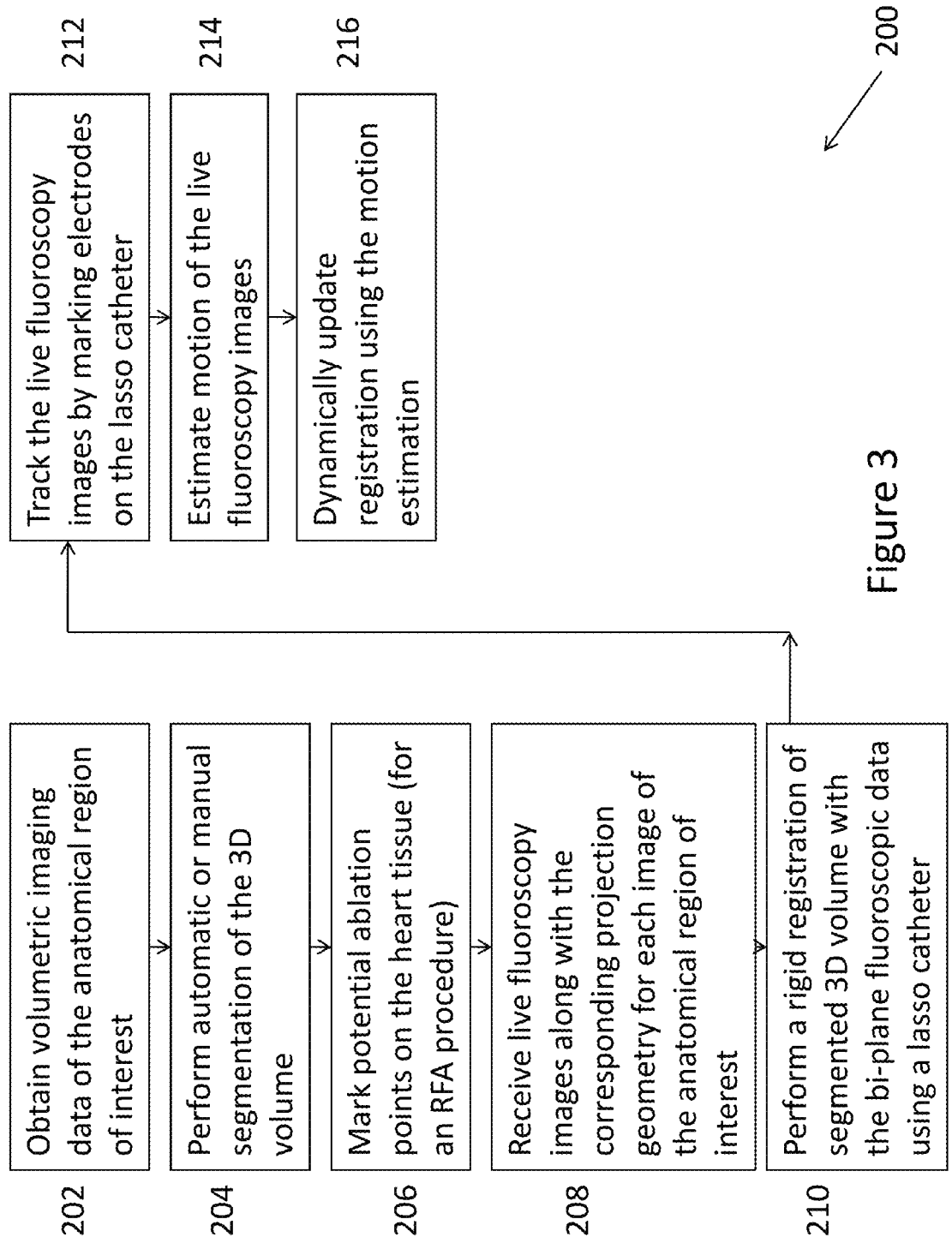
FIG. 3 is a simplified flowchart of a method for dynamically updating fluoroscopic overlays images carried out in accordance with an embodiment of the present invention.

FIG. 3 is a simplified flowchart of a method 200 for dynamically updating fluoroscopic overlays images carried out in accordance with an embodiment of the present invention. Generally, volumetric imaging data of the patient and, more particularly, of the anatomical region of interest (for example, the heart) is acquired (Step 202). Normally, this 3D data is acquired prior to the medical procedure to be performed (i.e., pre-operative) and may be acquired using CT or MR imaging. As an alternative, the data may be obtained from a 3D model of the anatomical region of interest. The method 200 performs automatic or manual segmentation of the 3D volume, which in this example would be the left atrium and pulmonary veins of the heart (Step 204). In the case of RFA, potential ablation points on the heart tissue may be marked (Step 206). It is also possible to refine the 3D scene further, e.g., by adding more models. These additional models can be generated either by additional interactive segmentation within the voxel data set or by reconstruction from two views (this is described in an article by Liron Yatziv, Julian Ibarz, Norbert Strobel, Saurabh Datta, and Guillermo Sapiro, entitled "Esophagus Silhouette Extraction and Reconstruction From Fluoroscopic Views for Cardiac Ablation Procedure Guidance", IEEE Transactions on Information Technology in Biomedicine, 2011, pp. 703-708, Vol. 15 (No. 5), which is incorporated by reference herein). The segmented 3D volume is then used as a basis for registration with real-time fluoroscopy data, which is acquired during the medical procedure (i.e., intra-operative).

In particular, the system 100 receives live fluoroscopy images along with the corresponding projection geometry for each image (Step 208) and a system 100 operator manually performs a rigid registration of the segmented 3D volume with the bi-plane fluoroscopic data (Step 210). During the medical procedure, a lasso catheter is secured to a pulmonary vein (PV) ostium. The catheter then moves along with the heart and is used to accomplish rigid registration. In doing this task, the lasso catheter has stable wall contact to ensure that residual signals can be detected and that a gapless isolation is achieved. A lasso catheter is a special catheter that can be fit into one of the pulmonary veins of the heart to allow for ablation on a series of points (this is described generally in an article by L. Gepstein, G. Hayam, and S. A. Ben-Haim, entitled "A Novel Method for Nonfluoroscopic Catheter-Based Electroanatomical Mapping of the Heart: In Vitro and In Vivo Accuracy Results," Circulation, 1997, pp 1611-1622, Vol. 95). If placed properly, the lasso catheter moves in sync with the left atrium (LA). Consequently, by tracking the lasso catheter, e.g., under bi-plane fluoroscopy, the 3D motion of both the lasso catheter and the live heart image can be estimated. This estimated motion can then be used to dynamically update fluoroscopy overlay images robustly and accurately (catheter tracking is described in an article by A. Brost, A. Wimmer, R. Liao, J. Hornegger, and N. Strobel, entitled "Catheter Tracking: FilterBased vs. Learning-Based," in Pattern Recognition, M. Goesele, S. Roth, A. Kuijper, B. Schiele, and K. Schindler, Eds., Lecture Notes in Computer Science 6376, 2010, pp. 293-302, Springer, Berlin/Heidelberg, which is incorporated by reference herein). Tracking under monoplane fluoroscopy also affords some motion compensation. Advantageously, a new lasso catheter tracking method may be used to allow for more robust and accurate dynamic overlays during EP procedures (this new method is described in more detail in an article by W. Wu, T. Chen, A. Barbu, P. Wang, N. Strobel, S. Zhou, and D. Comaniciu, entitled "Learning-based Hypothesis Fusion for Robust Catheter Tracking in 2D X-ray Fluoroscopy," IEEE Conference on Computer Vision and Pattern Recognition (CVPR), 2011, pp 1097-1104, which is incorporated by reference herein).

The operator performs the registration once the lasso catheter is secured to a pulmonary vein. Afterwards, the operator marks electrodes on the lasso catheter within the live fluoroscopy images to initiate the tracking of the live fluoroscopy images (Step 212). When tracking is active, the registration can be dynamically updated (Step 216) using the motion estimated from the lasso catheter (Step 214). Motion estimation in 3D requires simultaneous bi-plane fluoroscopy. If mono-plane images are available only, then planar shifts to the overlay can still be applied. More sophisticated mono-plane fluoroscopy methods are conceivable as well if a motion model is available (this is described in an article by Alexander Brost, Wen Wu, Martin Koch, Andreas Wimmer, Terrence Chen, Rui Liao, Joachim Hornegger, and Norbert Strobel, entitled "Combined Cardiac and Respiratory Motion Compensation for Atrial Fibrillation Ablation Procedures", Med Image Comput Comput Assist Interv. (MICCAI), 2011, pp. 540-7, 14(Pt. 1)).

A model-based approach may be used to track the user-marked lasso catheter electrodes within the fluoroscopy images (this is detailed in the above-cited Wu, et al. article). In such an approach, lasso catheter electrodes are detected as points parameterized by their position using trained probabilistic boosting tree (PBT) classifiers which are used for object classification and detection in an image. Specially-designed hypotheses based on the electrode detection results are fused. An effective hypothesis evaluation method, such as a Bayesian framework, is necessary to determine the exact position and shape of the lasso catheter. The goal is to maximize the posterior probability. More details can be found in the above-cited Wu, et al. article.

Once the centers of the lasso catheter (designated cA and cB) have been detected in both planes (regardless of the specific tracking approach), the method 200 may use the inverse of the projection matrices for both views (designated PA-1 and PB-1) to compute rays in 3D world coordinates. The median point of the nearest points of intersection between the two rays is taken as the new 3D position. This permits the motion of the catheter (and the live fluoroscopy images) to be estimated. The vector from the old position to the new position may then be used to shift the entire overlay in 3D.

Figure 4:
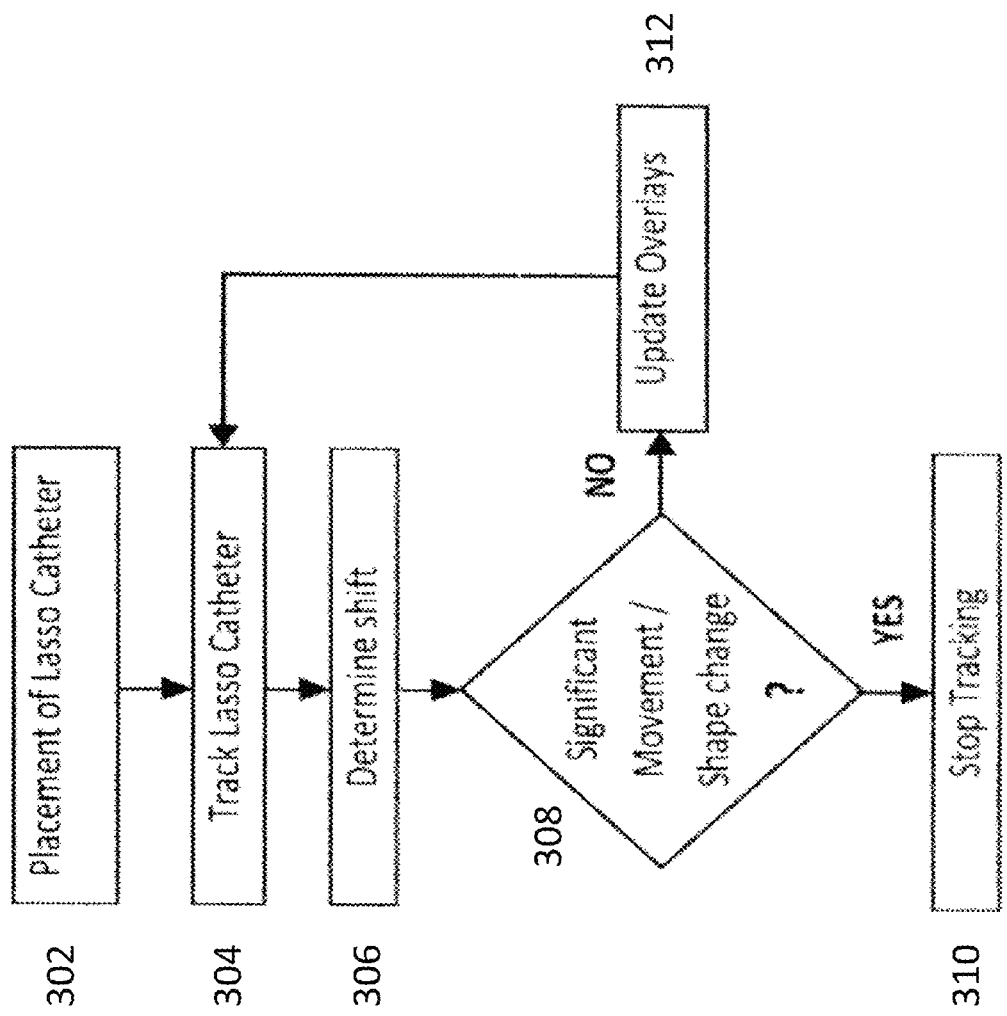
FIG. 4 is a simplified flowchart of another method for dynamically updating fluoroscopic overlays images carried out in accordance with an embodiment of the present invention.

The method 200 may be described as an overlay animation method and it is useful as long as the lasso catheter remains firmly positioned at the ostium of a pulmonary vein (PV). However, if a continuously tracked lasso catheter becomes detached and moves away from the PV, the animated fluoroscopy overlay image would follow the detached catheter unless precautions are taken. To avoid that the fluoroscopy overlay image is shown at the wrong position, a method is needed to tell the system 100 when to stop tracking Once tracking has been stopped, the overlay can be returned to its default initial position. Ideally, tracking should be stopped automatically to avoid added manual interface steps. Thus, the method 200 may also comprise a series of steps for stopping both the tracking of the lasso catheter and the performing of dynamic overlays based on the lasso catheter tracking. These additional steps may be performed manually by the system 100 operator, automatically by the system 100, or manually in part and automatically in part. FIG. 4 is a simplified flowchart of a method 300, carried out in accordance with an embodiment of the present invention, having several steps of the method 200 in performing dynamic registration along with these additional steps. Generally, the position and shape of the lasso catheter are quantities that can be directly obtained by the tracked electrodes. A constraint on the relative position and shape of the lasso catheter can then be used to automatically disable tracking (or to alert the operator to manually disable tracking) as outlined in FIG. 4.

As seen in the figure, the method 300 comprises the step of placing or securing the lasso catheter, for example, to a pulmonary vein (Step 302). Using an appropriate technique, the method 300 performs tracking of the electrodes of the lasso catheter, and the live fluoroscopy images (Step 304). Thereafter, the motion of the catheter (and the live fluoroscopy images) may be estimated by evaluating a shift of the catheter from a starting position to a new position (Step 306). Using the position and shape of the lasso catheter obtained by the tracked electrodes, the method 300 determines whether or not there are significant movements or shape changes of the lasso catheter that indicate that it is no longer attached to the vein (Step 308). In such cases, both the lasso catheter tracking and the display of an animated overlay image can be stopped automatically or via the operator (Step 310). The overlay image can then be returned into a default position. The detection of significant movement or shape change can be accomplished by several methods taking either or both the shape or movement of the lasso catheter into account. For example, the pulsatile movement of the heart results in a movement within a limited region of the fluoroscopic image. In the event that there is no detection of a significant movement or shape change, the method 300 may update the overlay image (Step 312) and continue the tracking of the lasso catheter (Step 304) and the process in general.

The use of a dynamic overlay and registration affords new visualization options for the system 100 for both overlays and 3D renderings. Traditional fluoroscopic images show the heart beating and patient movement while the table and background remains static. Within this view, the instruments inside the heart show synchronous movement with the heart beat even without active manipulation from the physician. This is referred to as a "table-coordinate" view of the information. Given a 3D image with fitted mesh and reconstructed 3D locations for catheters, a "table-coordinate" view would show similar movement of the heart (i.e., the mesh would be moving along with the instruments). A "patient coordinate" view is also possible where a "heart-centric" coordinate system is used. In this view, the patient's heart is considered fixed while all other elements are moving. Such a view can be potentially more useful than a "table-coordinate" view, especially in 3D. As an example of the usefulness, a "patient coordinate" view would show reduced or no movement of instruments when not manipulated by the physician. In 2D, this would show little or low motion for the ablation catheter and no motion for the lasso catheter. In a 3D mesh, any mesh obtained from the heart would be completely static while the catheter motion from the heart movement would be eliminated. This "patient coordinate" view can be extremely beneficial for showing movements induced only by the physician and not by the patient. The above methods of dynamic registration make this "patient coordinate" view possible since it allows for the coordinate system to be dynamically changed.

Figure 5:
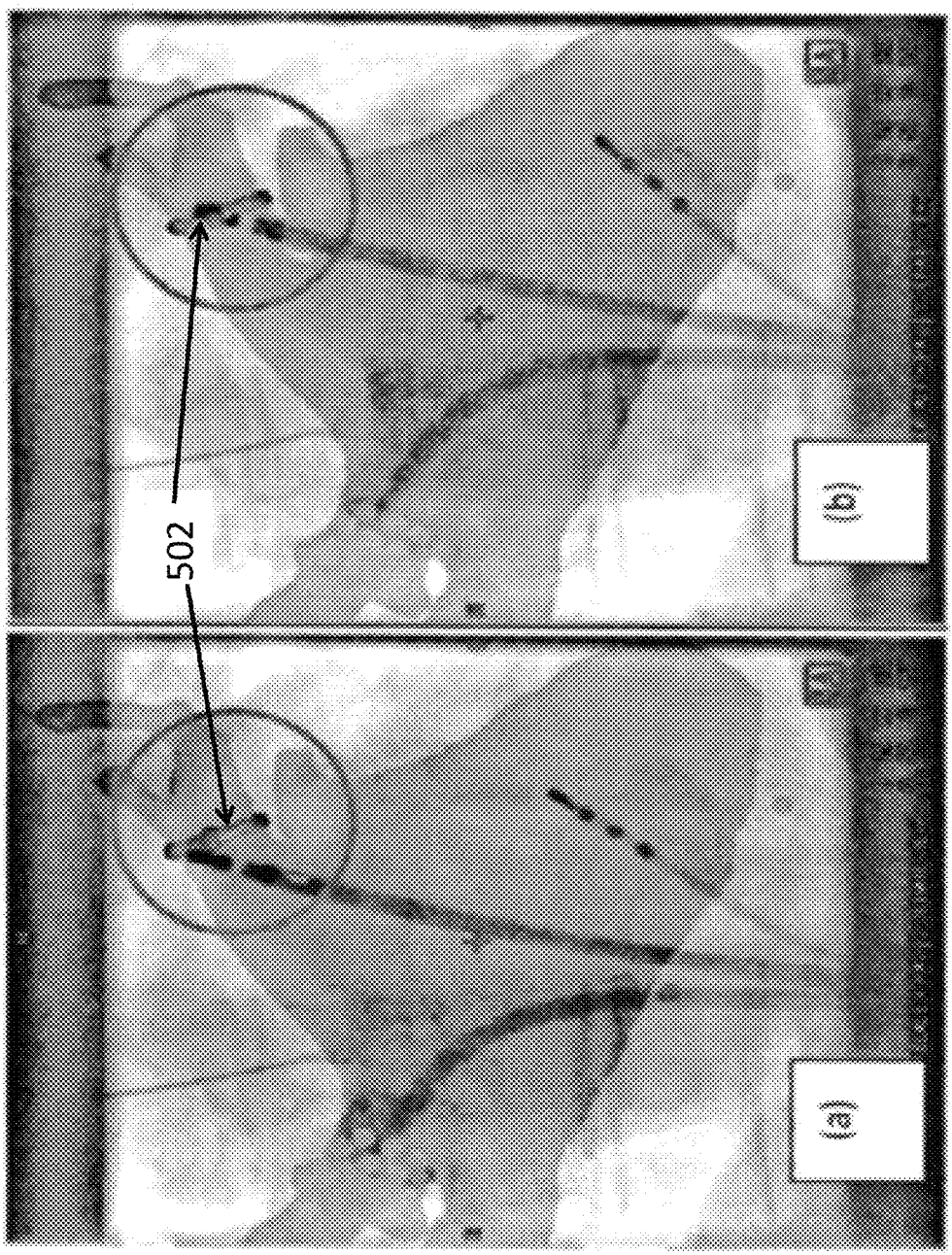
FIG. 5 is an image of a static overlay of a heart model shown at two different time points.
Figure 6:
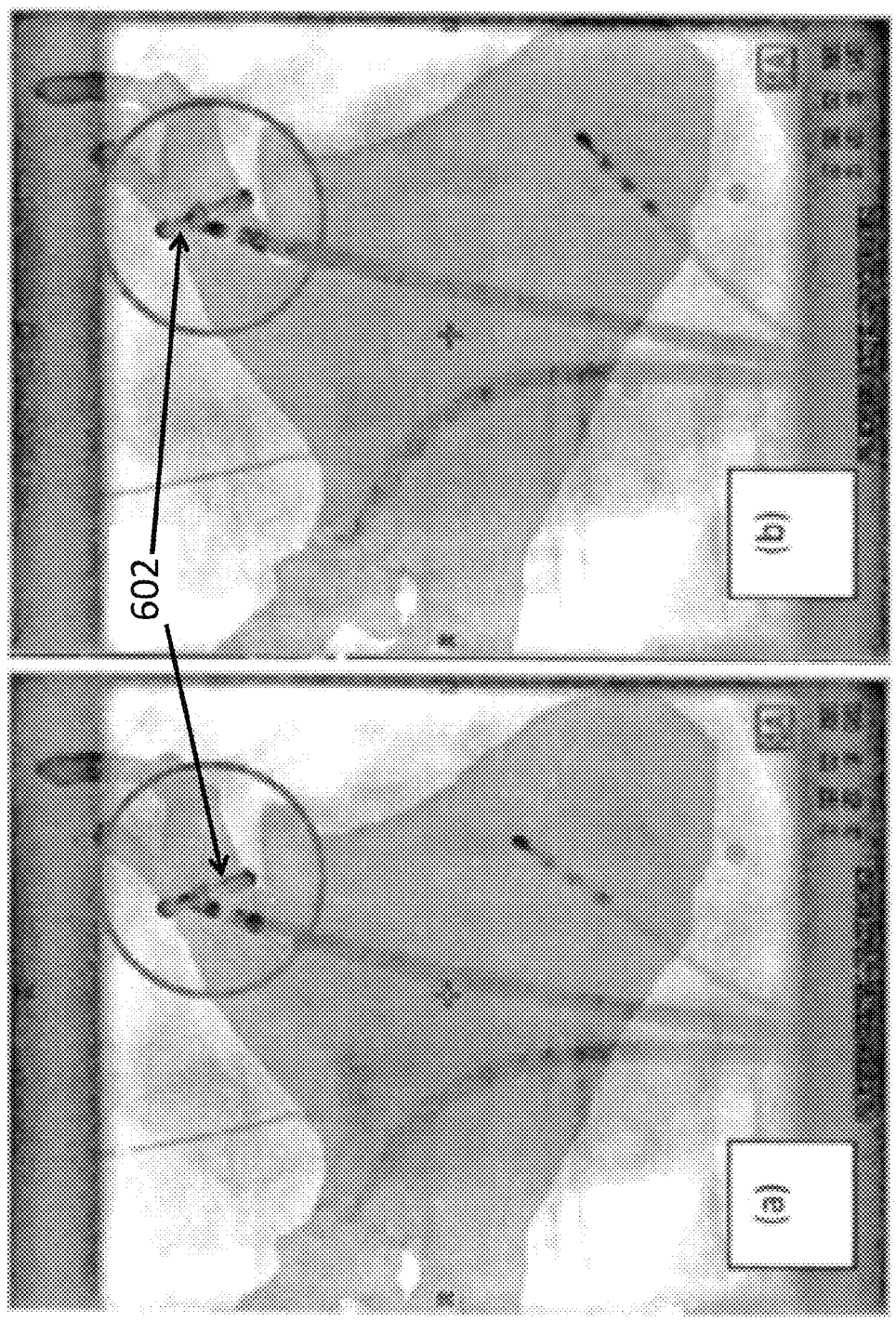
FIG. 6 is an image of a dynamically adjusted overlay of a heart model shown at two different time points.

The following describes the results of testing the accuracy of the above-described augmented fluoroscopy approaches 200, 300 based on ten pre-recorded fluoroscopic sequences. The 2D accuracy of the lasso catheter tracking was determined to be 0.65 mm on average in comparison to a manually created ground truth used for training. As no ground truth was available in 3D, accuracy was estimated based on the distance between the rays connecting the X-ray sources of the A-plane and the B-plane to the centers of the lasso catheter cA and cB, respectively. The results showed this error to be less than 1 mm. FIGS. 5 and 6 compare the overlay results. The framerate with bi-plane tracking and dynamic overlay updates was 3.5 frames per second on average. FIG. 5 is an image of a static overlay of a heart model and points of interest obtained from a pre-operative volume shown at two different time points (a) and (b). The circled region shows an ablation catheter 502 in the vicinity of ablation targets. Although the catheter 502 has not moved in relation to the heart, heart and breathing motion shifted the heart relative to the static overlay during the period between the two time points (a) and (b). This creates the appearance that the catheter 502 has moved slightly inside the heart. Although still useful for general guidance, this example demonstrates the limitations of static overlays. FIG. 6 shows an image of a dynamic overlay (i.e., dynamically adjusted overlay) of the heart model and points of interest obtained from a pre-operative volume shown at two different time points (a) and (b). Compared to the static overlays shown in FIG. 5, the position of a catheter 602 in relation to the marked points remains more stable than the catheter 502 in FIG. 5, allowing for more accurate guidance.

Other modifications are possible within the scope of the invention. For example, the subject to be scanned may be an animal subject or any other suitable object rather than a human patient.

Also, although the steps of the methods 200, 300 have been described in a specific sequence, the order of the steps may be re-ordered in part or in whole and the steps may be modified, supplemented, or omitted as appropriate. Also, the methods 200, 300 may use various well known algorithms and software applications to implement the steps and substeps. Further, the methods 200, 300 may be implemented in a variety of algorithms and software applications. Further, the methods 200, 300 may be supplemented by additional steps or techniques. It is also understood that the methods 200, 300 may carry out all or any of the steps using real-time data, stored data from a data archive or database, data from a remote computer network, or a mix of data sources.

Also, the various described instrumentation and tools may be configured and interconnected in various ways as necessary or as desired. Further, although in the described methods 200, 300 the user may use self-contained instrumentation and tools, the user may use other instrumentation or tools in combination with or in place of the instrumentation and tools described for any step or all the steps of the methods 200, 300, including those that may be made available via telecommunication means. Further, the described methods 200, 300, or any steps, may be carried out automatically by appropriate instrumentation and tools or with some manual intervention.

What is claimed is:

1. A method of dynamically updating overlay images on fluoroscopic images to aid in medical procedures, comprising:

a. securing a lasso catheter to a first anatomical structure of a first person that allows the lasso catheter to move in synchronization with a second anatomical structure of the first person;

b. performing a rigid registration of an overlay image with real-time fluoroscopic images of the first and second anatomical structures using the lasso catheter;

c. tracking movement of the lasso catheter and the real-time fluoroscopic images of the first and second anatomical structures and estimating the motion of the lasso catheter and the real-time fluoroscopic images of the first and second anatomical structures;

d. determining from the tracking and estimating step whether or not the lasso catheter is no longer secured to the first anatomical structure;

e. stopping tracking and estimating if it is determined that the lasso catheter is no longer secured to the first anatomical structure, or updating registration of the overlay image with the real-time fluoroscopic images if it is determined that the lasso catheter is secured to the first anatomical structure;

f. continuing the steps of c-e upon updating registration of the overlay image with the real-time fluoroscopic images; and g. fixing the second anatomical structure such that it does not move and does not impact motion of the lasso catheter so that movements of the lasso catheter only induced by a second person other than the first person are shown when steps c-f are continued.

2. The method of claim 1, wherein the first anatomical structure comprises a pulmonary vein and the second anatomical structure comprises the heart.

3. The method of claim 1, wherein the overlay image comprises a segmented 3D volume of the first and second anatomical structures and the real-time fluoroscopic images comprise bi-plane real-time fluoroscopic images of the first and second anatomical structures.

4. The method of claim 1, wherein tracking comprises marking electrodes of the lasso catheter and tracking the electrodes within the real-time fluoroscopic images using a model-based approach.

5. The method of claim 1, wherein estimating comprises evaluating positional shifts of the lasso catheter.

6. The method of claim 1, wherein the overlay image is returned to its initial position relative to the real-time fluoroscopic images upon stopping tracking and estimating.

7. The method of claim 1, wherein the lasso catheter is no longer secured to the first anatomical structure when it is outside a predetermined region of a real-time fluoroscopic image.

* * * * *